United States Patent [19]

Baur et al.

[11] Patent Number: 5,563,016
[45] Date of Patent: Oct. 8, 1996

[54] DIALLYLAMMONIUM COMPOUNDS, PROCESSES FOR THEIR PREPARATION AND THEIR USE

[75] Inventors: Rüdiger Baur, Eppstein/Taunus; Hans-Tobias Macholdt, Darmstadt, both of Germany

[73] Assignee: Hoechst AG, Frankfurt Am Main, Germany

[21] Appl. No.: 463,349

[22] Filed: Jun. 5, 1995

[30] Foreign Application Priority Data

Dec. 21, 1991 [DE] Germany ............... 41 42 541.3

[51] Int. Cl.$^6$ ................................................ G03G 5/00
[52] U.S. Cl. ................................ 430/110; 524/236
[58] Field of Search .................... 430/110; 524/236

[56] References Cited

U.S. PATENT DOCUMENTS

| | | | |
|---|---|---|---|
| 4,057,426 | 11/1977 | Mammino et al. | 430/120 |
| 4,400,396 | 8/1983 | Alvarez et al. | 424/325 |
| 4,496,643 | 1/1985 | Wilson et al. | 430/110 |
| 4,656,112 | 4/1987 | Kawagishi et al. | 430/110 |
| 4,670,594 | 6/1987 | Aigner et al. | 564/296 |
| 4,683,188 | 7/1987 | Suzuki et al. | 430/110 |
| 4,684,596 | 8/1987 | Bosner et al. | 430/110 |
| 4,877,885 | 10/1989 | Ballschuh et al. | 548/570 |
| 5,069,994 | 12/1991 | Gitzel et al. | 430/110 |

FOREIGN PATENT DOCUMENTS

| | | |
|---|---|---|
| 0053888 | 6/1982 | European Pat. Off. |
| 0284000 | 9/1988 | European Pat. Off. |
| 225128 | 7/1985 | Germany. |
| 224844 | 7/1985 | Germany. |
| 3528985 | 2/1987 | Germany. |
| 3837345 | 5/1990 | Germany. |

OTHER PUBLICATIONS

H. T. Macholdt, Dyes & Pigments 9 (1988) pp. 119–127. See AA.
Houben–Weyl, Bd.E 20/2, (1987) pp. 1023–1028.
Harada, Makromol. Chem. 107 (1967), 64.
Y. Negi, J.Polym.Sci. 5, (1967), 64.
Derwent Database, JP 600 26 346.
Derwent Database, JP 60 231 595.
Furton et al., J. Chromatogr., 399, 47–67 (1987).
Diaz, Carlos., Polyhedron 4(7), 1269–1270 (1985).
J. Van Overbéke et al., Bulletin De La Societe Chemique, 933–937 (1962).
T. E. Mead, J. Phys. Chem. 66:2149–2154. (1962).
Chemical Abstracts. vol. 61, No. 10, 11386, pp. 1743–1749 (1964).
Chemical Abstracts vol. 89, No. 13, 107937, (1978).
Patent Abstracts of Japan, JP 59 78 364 (1984).
Patent Abstracts of Japan, JP 63 23 167 (1988).
Patent Abstracts of Japan, JP 61 147 260 (1986).
Patent Abstracts of Japan, JP 61 258 270 (1987).
Patent Abstracts of Japan, JP 63 226 665 (1989).

*Primary Examiner*—Tae Yoon
*Attorney, Agent, or Firm*—Connolly and Hutz

[57] ABSTRACT

Ionic monomeric diallylammonium compounds having a targeted combination of diallylammonium cations with selected anions have particularly high and constant charge control properties and very good heat stabilities and dispersibilities.

The compounds according to the invention are outstandingly suitable for use as colorless charge control agents in toners and developers for electrophotographic recording processes and for use as charge-improving agents in powders and paints for surface coating, in particular in triboelectrically or electrokinetically sprayed powder paints.

23 Claims, No Drawings

DIALLYLAMMONIUM COMPOUNDS, PROCESSES FOR THEIR PREPARATION AND THEIR USE

The present invention relates to the technical field of charge control agents in toners and developers for electrophotographic recording processes and in powders and powder coatings for surface coating.

In electrophotographic recording processes, a "latent charge image" is produced on a photoconductor. This is effected, for example, by charging a photoconductor by means of a corona discharge and then subjecting the electrostatically charged surface of the photoconductor to imagewise exposure to light, the exposure causing the charge to drain to the earthed substrate at the exposed areas. The "latent charge image" thus produced is then developed by application of a toner. In the following step, the toner is transferred from the photoconductor onto, for example, paper, textiles, films or plastic, and is fixed, for example, by means of pressure, radiation, heat or the action of a solvent. The used photoconductor is then cleaned and is available for a new recording operation.

The optimization of toners is described in numerous patent specifications, the influence of the toner binder (variation of resin/resin components or wax/wax components), the influence of carriers (in two-component developers) and magnetic pigments (in one-component developers), inter alia, being investigated.

A measure of the toner quality is its specific charge q/m (charge per unit mass). In addition to the sign and level of the electrostatic charge, a decisive quality criterium above all is that the desired charge level is reached rapidly and that this charge remains constant over a relatively long activation period. In practice, this is of central importance inasmuch as the toner may be exposed to a considerable activation time in the developer mixture, before it is transferred to the photoconductor, since it sometimes remains in the developer mixture over a period for the production of up to several thousand copies. Moreover, the insensitivity of the toner to climatic influences, such as temperature and atmospheric humidity, is another important suitability criterion.

Both positively and negatively chargeable toners are used in copiers and laser printers, depending on the type of process and equipment.

To obtain electrophotographic toners or developers having either positive or negative charging, so-called charge control agents are often added. In addition to the sign of the charge control, the extent of the control effect is of importance, since a higher activity allows a smaller amount to be employed. Since toner binders as a rule show a marked dependence of the charging on the activation time, the task of a charge control agent is on the one hand to establish the sign and level of the toner charging, and on the other hand to counteract the drift in charging of the toner binder and to ensure that the charging of the toner retains constant. Charge control agents which cannot prevent the toner or developer from displaying a high charge drift over a prolonged period of use (aging), and which can even cause the toner or developer to undergo a reversal of charge, are therefore unsuitable in practice. Full-color copiers and laser printers operate by the principle of trichromism, which necessitates exact color shade matching of the three primary colors (yellow, cyan and magenta). The slightest shifts in color shade even of only one of the three primary colors necessarily requires a shift in the color shade of the other two colors so that full-color copies or prints faithful to the original can then also be produced. Because of this precise matching of the coloristic properties of the individual coloring agents to one another, which is necessary in color toners, charge control agents which have absolutely no intrinsic color are especially important.

In color toners, the three toners of yellow, cyan and magenta must also be matched exactly to one another in respect of their triboelectric properties, as well as meeting the precisely defined color requirements. This triboelectric matching is necessary, because in the case of a full-color print or full-color copy, the three color toners (or four color toners, when black is also included) must be transferred in the same apparatus in succession.

It is known that coloring agents can sometimes have a lasting influence on the triboelectric charging of toners (H.-T. Macholdt, A. Sieber, Dyes & Pigments 9 (1988), 119–127; U.S. Pat. No. 4,057,426). Because of the different triboelectric effects of coloring agents and the resulting, sometimes very marked influence on toner chargeability, it is not possible simply to add the coloring agents to a toner base recipe compiled once and for all. Rather, it may be necessary to compile an individual recipe for each coloring agent, for which, for example, the nature and amount of the required charge control agent are tailor-made specifically. This procedure is correspondingly expensive, and additionally accompanies the difficulties already described in the case of color toners for process color (trichromism). Highly active colorless charge control agents which are capable of compensating the different triboelectric properties of various coloring agents and of imparting the desired charging to the toner are therefore necessary. In this manner, coloring agents with very different triboelectric properties can be employed in the various toners required (yellow, cyan, magenta and, if appropriate, black) with the aid of a toner base recipe, compiled once and for all, with one and the same charge control agent. Moreover, it is important in practice for the charge control agents to have a high heat stability and be readily dispersible. Typical temperatures for incorporating charge control agents into the toner resins are between 100° C. and 200° C. when kneaders or extruders, for example, are used. A heat stability of 200° C., or even better 250° C., is accordingly of great advantage. It is also important for the heat stability to be guaranteed over a relatively long period of time (about 30 minutes) and in various binder systems. This is important, since matrix effects which occur again and again lead to premature decomposition of the charge control agent in the toner resin, which means that the toner resin becomes dark yellow or dark brown in color and the charge control effect is completely or partly lost. Typical toner binders are polymerization, polyaddition and polycondensation resins, such as, for example, styrene resins, styrene/acrylate resins, styrene/butadiene resins, acrylate resins, polyester resins, phenolic resins and epoxy resins, individually or in combination, which can also comprise other contents, such as coloring agents, waxes or flow auxiliaries, or to which these can be subsequently added. For a good dispersibility, it is of great advantage if the charge control agent as far as possible has no waxy properties, no tackiness and a melting or softening point of >150° C., preferably >200° C. Tackiness often leads to problems during metering into the toner formulation, and low melting or softening points can mean that no homogeneous distribution is achieved during dispersion, since the material merges, for example, in the form of droplets in the carrier material.

Apart from being used in electrophotographic toners and developers, charge control agents can also be employed for improving electrostatic charging of powders and coatings, in particular in triboelectrically or electrokinetically sprayed powder coatings, such as are used for surface coating of objects of, for example, metal, wood, plastic, glass, ceramic, concrete, textile material, paper or rubber. Powder coating technology is used, inter alia, for painting small objects, such as garden furniture, camping articles, domestic appliances, vehicle components, refrigerators and shelves, and for painting workpieces of complicated shape. The powder coating or the powder in general acquires its electrostatic charging by one of the following two processes:

a) in the corona process, the powder coating or the powder is led past a charged corona and is charged during this procedure, b) in the triboelectric or electrokinetic process, use is made of the principle of frictional electricity. In the spray unit, the powder coating or the powder acquires an electrostatic charging which is opposite to the charge of the friction partner, in general a hose or spray tube (for example of polytetrafluoroethylene).

A combination of the two processes is also possible.

Epoxy resins, polyester resins containing carboxyl and hydroxyl groups, polyurethane resins and acrylic resins, together with the corresponding curing agents, are typically employed as powder coating resins. Combinations of resins are also used. Thus, for example, epoxy resins are often employed in combination with polyester resins containing carboxyl and hydroxyl groups. Typical curing agent components for epoxy resins are, for example, acid anhydrides, imidazoles and dicyandiamide, and derivatives thereof. Typical curing agent components for polyester resins containing hydroxyl groups are, for example, acid anhydrides, masked isocyanates, bisacylurethanes, phenolic resins and melamine resins. Typical curing agent components for polyester resins containing carboxyl groups are, for example, triglycidyl isocyanurates or epoxy resins. Typical curing agent components which are used in acrylic resins are, for example, oxazolines, isocyanates, triglycidyl isocyanurates or dicarboxylic acids.

The disadvantage of inadequate charging is observed above all in powders and powder coatings, which are sprayed triboelectrically or electrokinetically and have been prepared on the basis of polyester resins, in particular polyesters containing carboxyl groups, or on the basis of so-called mixed powders, also called hybrid powders. Mixed powders are understood as meaning powder coatings, the resin base of which comprises a combination of epoxy resin and polyester resin containing carboxyl groups. The mixed powders form the basis for the powder coatings most frequently represented in practice. Inadequate charging of the abovementioned powders and powder coatings means that the deposition rate and throwing power on the workpiece to be coated are inadequate. (The term "throwing power" is a measure of the extent to which a powder or powder coating is deposited on the workpiece to be coated, including on the reverse sides, hollow spaces, crevices and, above all, on internal edges and corners.)

Colorless charge control agents are claimed in numerous patent specifications. However, the colorless charge control agents known to date have a number of disadvantages, which severely limit or sometimes render impossible use in practice. Thus, the chromium, iron, cobalt and zinc complexes described in U.S. Pat. No. 4,656,112 also have, in addition to the problems of heavy metals, the disadvantage that they are sometimes not really colorless, and can therefore be used to only a limited extent in color toners or in white or colored powder coatings. The known quaternary ammonium compounds, which are suitable per se, are often difficult to disperse, which leads to non-uniform charging of the toner. Furthermore, the problem often arises that the toner charge produced by these compounds is not stable over a relatively long activation period (activation time of up to 24 hours), especially at a high temperature and atmospheric humidity, which then leads to enrichment of wrongly or inadequately charged toner particles in the course of a copying or printing process, and therefore brings the process to a standstill.

It is furthermore known that ammonium- and immonium-based charge control agents can be sensitive to light or mechanical effects (U.S. Pat. No. 4,683,188) and can be unstable to heat, and that they form decomposition products which can have an adverse effect on the triboelectric charging of the toner (U.S. Pat. No. 4,684,596) and/or have a deep, often dark brown, intrinsic color. Moreover, they often have waxy properties, are sometimes water-soluble and/or have a low activity as charge control agents.

Charge control agents which are suitable per se and are based on highly fluorinated ammonium and immonium compounds (U.S. Pat. No. 5,069,994) have the disadvantage of an involved synthesis, which gives rise to high preparation costs for the corresponding substances, and are not sufficiently heat-stable. Phosphonium salts are less active as charge control agents than ammonium salts (U.S. Pat. No. 4,496,643), and may cause toxicological problems.

Charge control agents based on polymeric ammonium compounds sometimes lead to an amine smell in the toner or developer, and the charge control properties of these substances may change due to relatively easy oxidation and absorption of moisture. Moreover, the oxidation products are colored and therefore cause trouble, above all in color toners.

The abovementioned charge control agents for electrophotographic toners and developers are unsuitable for use in the predominantly white or clear powders and powder coatings sprayed triboelectrically or electrokinetically, for example, because of their color. Furthermore, a lack of heat stability severely limits the use of such charge control agents, since powder coatings are stored, for example, at above 200° C for 15 minutes. The charge control agents claimed in U.S. Pat. No. 5,069,994 for powders and powder coatings are difficult to handle because of their waxy nature and water-solubility or hygroscopic nature, and can be used to only a limited extent.

The aim of the present invention is therefore to discover improved, particularly active, colorless charge control agents, with which, in addition to ensuring the charge level, it must be ensured that this charge is reached rapidly and is constant, and the charge control agent should not be sensitive to changes in temperature and atmospheric humidity. Moreover, these compounds should be highly heat stable, above all also in the particular carrier material (resin) over a relatively long period of time, and as far as possible water-insoluble, readily dispersible and compatible with the contents of the toner or powder paint. Furthermore, synthesis of the compounds should be not very involved, and their preparation should be inexpensive.

Surprisingly, it has now been found that monomeric diallylammonium compounds have particularly high and constant charge control properties and very good heat stabilities and dispersibilities by targeted combination of the diallylammonium cations with selected anions.

The present invention relates to ionic monomeric diallylammonium compounds of the formula (I)

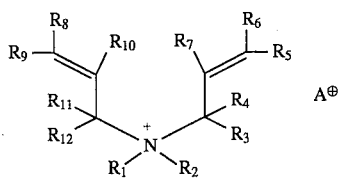 (I)

and mixtures or mixed crystals thereof, in which the radicals $R_1$ to $R_{12}$ independently of one another are each a hydrogen atom, a halogen atom, a hydroxyl radical, a primary, secondary or tertiary amino radical, a carboxylic acid or carboxylic acid ester radical, an acyl radical, a sulfonic acid or sulfonic acid ester radical, a cyano radical or a nitro radical, or are in each case a radical based on an aliphatic or aromatic hydrocarbon, which can be interrupted by hetero atoms, and $A^{\ominus}$ is in each case the stoichiometric equivalent of an inorganic anion, of an anion of a heteropolyacid or of a borate of the formula (II)

 (II)

in which the radicals $R_{13}$ to $R_{16}$ on the borate anion independently of one another are aliphatic or cycloaliphatic radicals, or aryl or heteroaryl or aralkyl radicals, it being possible for these radicals to be substituted by alkyl ($C_1$–$C_4$), alkoxy($C_1$–$C_4$) or aryl radicals or by halogen atoms, or are fluorine atoms, or of an organic anion, preferably based on a phenolate, olefinic, aliphatic or aromatic carboxylate, thiolate, sulfonate or sulfate, in which the alkyl, alkenyl or aryl radicals can also be perfluorinated, or based on a disulfo-pyrrolidinium-betaine of the formula (III)

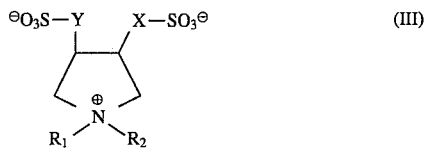 (III)

in which $R_1'$ and $R_2'$ have the meanings given for $R_1$ and $R_2$, and X and Y are in each case a straight-chain or branched aliphatic, saturated or unsaturated alkyl($C_1$–$C_{18}$) radical or alkoxy($C_1$–$C_{18}$) radical, or $A^{\ominus}$ is a combination of these anions; and mixtures of these compounds and mixed crystals with mixed anions and/or cations.

Inorganic anions $A^{\ominus}$ which are employed according to the invention are, for example, $F^-$, $I^-$, $NO_3^-$, $OH^-$, $HSO_4^-$, $S_2^-$, $SO_3^{2-}$, $S_2O_3^{2-}$, $HCO_3^-$, $CO_3^{2-}$, $H_2PO_4^-$, $HPO_4^{2-}$, $PO_4^{3-}$, $CN^-$, cyanate, isocyanate, thiocyanate, zinc tetracyanate, zinc tetrathiocyanate, perchlorate, $PF_6^-$, molybdates, such as $MoO_4^{2-}$, thiomolybdates, such as $MoS_4^{2-}$, or tungstates, such $WO_4^{2-}$. However, a combination of these anions is also possible, in particular also in combination with $Cl^-$, $Br^-$ or $SO_4^{2-}$.

Molybdatophosphates, such as $P(Mo_3O_{10})_4^{3-}$, tungstophosphates, such as $P(W_3O_{10})_4^{3-}$, or silicomolybdates, for example, are employed according to the invention as an anion of a heteropolyacid.

Borates which are employed according to the invention are, preferably, tetrafluoborate, tetrachloroborate, tetraphenylborate, tetra(fluorophenyl)borate, tetra(chlorophenyl)borate, tetratolylborate, tetranaphthylborate, tetra(methoxyphenyl)borate, tetrabiphenylborate, tetrabenzylborate or tetrapyridylborate.

Organic anions $A^{\ominus}$ which are employed according to the invention are, for example, ethyl sulfate, thiolate, phenolate, nitrophenolate, saturated or unsaturated aliphatic or cycloaliphatic or aromatic carboxylate or sulfonate, preferably acetate, lactate, benzoate, the mono- or dianion of dithiodibenzoic acid, salicylate, 2-hydroxy-3-naphthoate, 2-hydroxy-6-naphthoate, ethyl-sulfonate, phenylsulfonate or tosylate, and furthermore perfluorinated saturated or unsaturated aliphatic or cycloaliphatic or aromatic carboxylate or sulfonate, preferably perfluoroacetate, perfluoro($C_1$–$C_{30}$)alkyl-benzoate, perfluoroethylsulfonate or perfluoro($C_1$–$C_{30}$)-alkylbenzenesulfonate, and saturated or unsaturated aliphatic or cycloaliphatic or aromatic di- or tricarboxylate, preferably citrate, oxalate or succinate, or di- or trisulfonate, chlorinated and fluorinated aliphatic, cycloaliphatic or aromatic carboxylates, such as trifluoroacetate, and disulfo-pyrrolidinium-betaines of the formula (III) in which $R_1'$ and $R_2'$ are $R_1$ and $R_2$, and X and Y are straight-chain or branched aliphatic, saturated or unsaturated alkyl ($C_1$–$C_{18}$) or alkoxy($C_1$–$C_{18}$) radicals, preferably alkyl($C_1$–$C_5$) or alkoxy($C_1$–$C_5$) radicals, polyoxyalkylene radicals, preferably polyoxyethylene and polyoxypropylene radicals, of the formula (alkylene($C_1$–$C_5$)—O)$_n$—R, in which R is a hydrogen atom or an alkyl($C_1$–$C_4$) radical and n is a number from 1 to 10.

Compounds of the formula (I) which are preferred in the context of the present invention are those in which $A^{\ominus}$ is an anion from the group comprising $F^-$, $I^-$, $BF_4^-$, $B(aryl)_4^-$, $PF_6^-$ or $P(Mo_3O_{10})_4^{3-}$, or of a disulfopyrrolidinium-betaine of the formula (III);

$R_1$ and $R_2'$, and $R_1'$ and $R_2'$ independently of one another are hydrogen atoms, straight-chain or branched, saturated or unsaturated alkyl($C_1$–$C_{18}$) or alkoxy($C_1$–$C_{18}$) radicals, polyoxyalkylene radicals, preferably polyoxyethylene and/or polyoxypropylene radicals, of the formula (alkylene($C_1$–$C_5$)—O)$_n$—R, in which R is a hydrogen atom, an alkyl ($C_1$–$C_4$) radical or an acyl radical, preferably the acetyl, benzoyl or naphthoyl radical, and n is a number from 1 to 10; aryl or heteroaryl radicals, preferably phenyl, naphthyl or pyridyl radicals; aralkyl radicals, preferably tolyl radicals; aralkoxy radicals, preferably methoxyphenyl radicals; alkaryl radicals, preferably benzyl radicals; or cycloalkyl radicals, preferably cyclopentyl or cyclohexyl radicals, or the abovementioned radicals can contain at least one hetero atom, preferably nitrogen, oxygen, sulfur, phosphorus or a combination thereof, and can be substituted by one or more carboxamide radicals, sulfonamide radicals, urethane radicals, ketone radicals, primary, secondary or tertiary amino radicals, nitro radicals, ether radicals, in particular alkylene ($C_2$–$C_4$)—O-alkyl ($C_1$–$C_4$) radicals, alkyl ($C_1$–$C_4$) radicals, alkoxy($C_1$–$C_4$) radicals, aroxy radicals, in particular phenoxy radicals, halogenoalkyl($C_1$–$C_{30}$) radicals, halogenoalkoxy($C_1$–$C_{30}$) radicals or ester radicals, in particular —C(O)O-alkyl($C_1$–$C_4$), one or more halogen atoms or hydroxyl, carboxyl, sulfonic acid, cyano or mercapto groups, or a combination thereof, or $R_1$ and $R_2$, and $R_1'$ and $R_2'$ together form a saturated or unsaturated, aromatic or non-aromatic 5- to 7-membered ring system, preferably the pyridinium ring system, which can contain further hereto atoms, preferably nitrogen, oxygen, sulfur or a combination thereof, in the ring, in particular the morpholinium ring system, and which can be substituted and/or modified by condensation of or bridging to other ring systems, in particular the quinolinium ring system; and $R_3$ to $R_{12}$ independently of one another have the meanings given above for $R_1$ and $R_2$, and $R_1'$ and $R_2'$, or are halogen atoms or aroxy radicals, preferably phenoxy radicals; and mixtures of these compounds and mixed crystals with mixed anions and/or cations.

Compounds of the formula (I) which are particularly preferred in the context of the present invention are those in which $A^\ominus$ is an anion from the group comprising $BF_4^-$ and $B(aryl)_4^-$, in which aryl is phenyl, naphthyl, fluorophenyl, chlorophenyl, methoxyphenyl, biphenyl, pyridyl or tolyl or a combination thereof;

$R_1$ and $R_2$ independently of one another are hydrogen atoms, straight-chain or branched, saturated or unsaturated alkyl($C_1$–$C_8$) or alkoxy($C_1$–$C_8$) radicals, aryl or heteroaryl radicals, in particular phenyl, naphthyl or pyridyl radicals, aralkyl radicals, in particular tolyl radicals, aralkoxy radicals, in particular methoxyphenyl radicals, alkaryl radicals, in particular benzyl radicals, or cycloalkyl radicals, in particular cyclopentyl or cyclohexyl radicals, it being possible for the radicals $R_1$ and $R_2$ to be substituted by one or more halogen atoms, hydroxyl, carboxyl, sulfonic acid or carboxamide radicals, in particular —NH—C(O)-alkyl ($C_1$–$C_4$), sulfonamide radicals, in particular —NH—$SO_2$-alkyl ($C_1$–$C_4$), keto radicals, in particular —C(O)-alkyl($C_1$–$C_4$), primary, secondary or tertiary amino radicals, in particular —$NH_2$, —NH[alkyl($C_1$–$C_4$)]— or —N[alkyl($C_1$–$C_4$)]$_2$, nitro radicals, ether radicals, in particular alkylene($C_2$–$C_4$)—O-alkyl($C_1$–$C_4$), alkyl($C_1$–$C_4$) radicals, alkoxy($C_1$–$C_4$) radicals, aroxy radicals, in particular phenoxy radicals, halogenoalkyl($C_1$–$C_4$) radicals, halogenoalkoxy($C_1$–$C_4$) radicals or ester radicals, in particular —C(O)O-alkyl($C_1$–$C_4$); and $R_3$ to $R_{12}$ independently of one another have the meanings given above for $R_1$ and $R_2$, or are halogen atoms, and mixtures of these compounds and mixed crystals with mixed anions and/or cations.

Compounds which are especially preferred in the context of the present invention are those of types (1) to (7)

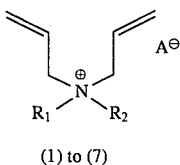

(1) to (7)

in which in compound (1), $A^\ominus$ has the meanings $BF_4^-$ or $B(phenyl)_4^-$, $R_1$ has the meanings H or $CH_3$ and $R_2$ has the meanings $CH_3$, $C_8H_{17}$ or H;

in compound (2), $A^\ominus$ is an alkyl-3 4-disulfomethyl-pyrrolidinium-betaine of the formula (III), in which X and Y are in each case alkyl($C_1$–$C_5$) and $R_1'$ and $R_2'$ are in each case H or $CH_3$, and any desired mixtures or mixed crystals of compounds types (1) and (2);

in compound (3), $A^\ominus$ has the meaning $BF_4^-$;

in compound (4), $A^\ominus$ has the meaning $B(C_6H_5)_4^-$, in compound (5), $A^\ominus$ has the meaning $PF_6^-$, in compound (6), $A^\ominus$ has the meaning 1,1-dialkyl-3,4-disulfomethyl-pyrrolidinium-betaine, and in compound (7), $A^\ominus$ has the meaning $P(Mo_3O_{10})_4^{3-}$.

The invention furthermore relates to a process for the preparation of the compounds of the formula (I) by anion exchange. The preparation is carried out by adding one or more compound(s) on which the anion $A^\ominus$ is based, preferably the sodium salt, to a diallylammonium halide of the formula (IV)

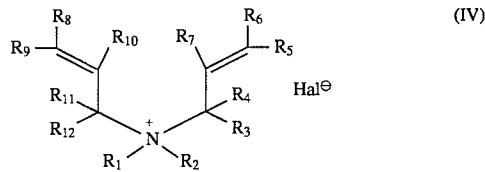

in which Hal is fluorine, chlorine, bromine or iodine, preferably chlorine or bromine, particularly preferably chlorine, as a solution in water or in a mixture of water and an organic solvent which is completely or partly miscible with water, at a temperature between 0° C. and 100° C., preferably 10° C. and 70° C., and a pH of between 3 and 10, preferably 5 and 8, and then, if appropriate, precipitating the compound of the formula (I) according to the invention by salting out with halogen-containing salts, for example potassium chloride. As a rule, the compounds according to the invention are so sparingly soluble in water or in the water-solvent mixture mentioned that they also precipitate out of the solution without additional salting out. The preparation of the starting compounds, the diallylammonium chlorides, is known and is described in detail in the literature [for example Houben-Weyl, "Methoden der Organischen Chemie (Methods of Organic Chemistry)", volume E20/2, Thieme-Verlag, Stuttgart, 1987, 1023–1028; S. Harada and K. Arai, Makromol. Chem. 107, (1967) 64; Y. Negi, S. Harada and O. Ishizuka, J. Polym. Sci. 5, (1967) 64; and U.S. Pat. No. 4,670,594]. The compounds are prepared, for example, by reaction of allyl halides with N,N-dialkylallylamines and quaternization of the diallylamine.

The corresponding Na sulfo-betaine (III) can be obtained in accordance with U.S. Pat. No. 4,877,885.

In a preferred embodiment, the anion exchange is carried out in a mixture of water and isopropanol, water and isobutanol or water and methyl isobutyl ketone.

In another preferred embodiment, the diallylammonium chloride is reacted with sodium tetraphenylborate, sodium tetra-o-fluorophenylborate, sodium tetra-m-fluorophenylborate, sodium tetra-p-fluorophenylborate, sodium tetra-o-chlorophenylborate, sodium tetra-m-chlorophenylborate, sodium tetra-p-chlorophenylborate, sodium tetra-o-tolylborate, sodium tetra-m-tolylborate, sodium tetra-p-tolylborate, sodium tetra-1-naphthylborate, sodium tetra-2-naphthylborate, sodium tetra-o-methoxyphenylborate, sodium tetra-m-methoxyphenylborate, sodium tetra-p-methoxyphenylborate, sodium tetra-o-biphenylborate, sodium tetra-m-biphenylborate, sodium tetra-p-biphenylborate, sodium tetrabenzylborate, sodium tetra-o-pyridylborate, sodium tetra-m-pyridylborate, sodium p-pyridylborate or sodium tetrafluoroborate.

The compounds according to the invention are colorless and, by the targeted combination of certain monomeric diallylammonium cations with selected anions, have particularly high and constant charge control properties and very good heat stabilities and dispersibilities.

A great industrial advantage of these readily dispersible compounds is that substances of the same class of compound can be employed either as positive or as negative charge control agents, depending on the carrier/resin combination. Either positive or negative toners can thus be prepared with the aid of a fixed toner base recipe (comprising toner binders, coloring agents, flow auxiliaries and, if appropriate, other components), by choosing the desired carrier and/or resin and by a suitable cation/anion combination in the compounds according to the invention.

The synthesis, which is not very involved, the inexpensive preparation, the high activity, the excellent heat stability and, in particular, the achievement of a significantly improved deposition rate and throwing power are of quite particular advantage in the case of the compounds according to the invention, so that overall a more efficient and more economical utilization of sprayed powder paints results.

The invention furthermore relates to the use of the compounds according to the invention and of the compounds of the formula (I) in which the anion $A^\ominus$ can also be chloride, bromide or sulfate, in addition to the meanings mentioned, as charge control agents, individually or in combination, in electrophotographic toners and developers which are employed for copying or duplicating masters and for printing electronically, magnetically or optically stored information or in colorproofing. The compounds according to the invention moreover are suitable as charge-improving agents in powders and paints for surface coating of objects of metal, wood, plastic, glass, ceramic, concrete, textile material, paper or rubber, in particular in triboelectrically or electrokinetically sprayed powder coatings. These compounds furthermore can also be employed as charge-improving agents in the form of coatings of carriers or a constituent of coatings of carriers which are used in developers for electrophotographic copying or duplication of masters and for printing electronically, optically or magnetically stored information or in colorproofing.

The particular advantage of the compounds claimed according to the invention is that they are colorless and have a high charge control effect, and that this is constant over a relatively long activation period (up to 24 hours).

Thus, for example, a test toner comprising 1 percent by weight of the compound of type (4) shows a charging of −19 µC/g after 10 minutes, −18 µC/g after 30 minutes, −15 µC/g after 2 hours and −15 µC/g after 24 hours (Use Example 1).

A test powder coating comprising 1 percent by weight of compound (4) shows a charging of +3 µC/g after 10 minutes, +4 µC/g after 30 minutes, +7 µC/g after 2 hours and 6 µC/g after 24 hours (Use Example 5).

The high charge control effect becomes clearer if, for comparison, the charging properties of the pure toner binder, for example ®Dialec S-309, are considered: (Comparison Example 1): −4 µC/g after 10 minutes, −12 µC/g after 30 minutes, −27 µC/g after 2 hours, −48 µC/g after 24 hours; or those of a pure powder coating binder, for example ®Crylcoat 430, are considered (Comparison Example 2): −20 µC/g after 10 minutes, −15 µC/g after 30 minutes, −8 µC/g after 2 hours, −4 µC/g after 24 hours.

It is of great importance in practice that the compounds according to the invention are chemically inert and are readily compatible with binders, for example styrene acrylates, polyesters, epoxides and polyurethanes. Furthermore, the compounds are heat-stable and can therefore be incorporated into the customary binders by the customary processes (extrusion, kneading) under the usual conditions (temperatures of between 100° C. and 200° C.) without difficulty. The synthesis of the compounds according to the invention is not very involved, and the products are obtained in high purity.

The compounds used according to the invention are as a rule homogeneously incorporated in a concentration of about 0.01 to about 30 percent by weight, preferably about 0.1 to 5.0 percent by weight, into the binder of the particular toner, developer, paint or powder coating, for example by extrusion or kneading.

The charge control agents for toners or charge-improving agents for powders and paints for surface coating, in particular for triboelectrically or electrokinetically sprayed powder coatings, can be added here as dried and ground powders, dispersions or solutions, press-cakes or a masterbatch, as compounds applied to suitable carriers, such as, for example, silica gel, $TiO_2$ or $Al_2O_3$, from an aqueous or non-aqueous solution, or in another form. In principle, the compounds employed according to the invention can likewise also already be added during preparation of the particular binder, that is to say in the course of polymerization, polyaddition or polycondensation thereof.

The level of electrostatic charging of the electrophotographic toners or of the powder coatings in which the charge control agents according to the invention have been incorporated homogeneously was measured on standard test systems under identical conditions (such as the same dispersing times, same particle size distribution and same particle form) at about 20° C. and 50% relative atmospheric humidity. The electrostatic charging of the toner or powder coating was effected by swirling with a carrier, i.e. a standardized friction partner (3 parts by weight of toner per 97 parts by weight of carrier), on a roller unit (150 revolutions per minute). The electrostatic charging was then measured on a customary q/m measuring stand (J. H. Dessauer, H. E. Clark, "Xerography and related Processes", Focal Press, N.Y., 1965, page 289; and J. F. Hughes, "Electrostatic Powder Coating", Research Studies Press Ltd., Letchworth, Hertfordshire, England, 1984, Chapter 2). The particle size has a great influence in the determination of the q/m value, which is why strict attention was paid to a uniform particle size distribution in the toner and powder coating samples obtained by sifting. An average particle size of 10 µm is thus aimed at for toners, while an average particle size of 50 µm is practicable for powder coatings.

The tribospraying of the powders and powder coatings was carried out with a spray apparatus, for example ®Tribo Star from Intec (Dortmund), using a standard spray pipe and star-shaped insert at maximum powder throughput with a spraying pressure of 3 bar. For this, the object to be sprayed was suspended in a spray cabin and sprayed directly from the front, without further movement of the spray apparatus, from a distance of about 20 cm. The particular charging of the sprayed powder was then measured with a "measuring instrument for measurement of the triboelectric charge of powders" from Intect (Dortmund). For the measurement, the measurement antenna of the measuring instrument was held directly in the cloud of powder emerging from the spray apparatus. The current strength resulting from the electrostatic charge of the powder coating or powder was displayed in µA. The deposition rate was then determined in % by determining the difference in weight between the sprayed and deposited powder paint.

The following examples serve to illustrate the invention, without limiting it to these. The term "min" means "minutes" and "h" means "hours".

Preparation Example 1

Compound (4)

67.36 g (0.25 mol) of a 60% strength by weight aqueous diallylammonium chloride solution were introduced into 1000 ml of deionized water. 92.24 g (0.25 mol) of NaB(C$_6$H$_5$)$_4$ were added to the solution at 50° to 60° C. in the course of 3 min, while stirring intensively. A voluminous white precipitate occurred. The suspension was subsequently stirred at 50° C. for 10 min and cooled to about 20° C., and the solid was filtered off with suction and rinsed intensively several times. Finally, the substance was dried in vacuo under 200 mbar at 90° C.

Yield: 111.07 g (99% of theory) Decomposition: 240° C. Elemental analysis: C 86.0%; H 8.0%; N 3.2%; B 2.6% (found) C 86.6%; H 7.9%; N 3.1%; B 3.0% (calculated)

Preparation Example 2

Compound (7)

A saturated solution of 94.5 g (0.045 mol) of Na$_3$P[Mo$_3$O$_{10}$]$_4$ in 210 ml of water was added to 40.0 g (0.15 mol) of a 60% strength by weight aqueous diallylammonium chloride solution at about 20° C. The suspension formed was subsequently stirred for 10 min, and the solid was filtered off with suction and washed with cold water until free from chloride. Finally, the substance was dried in vacuo under 200 mbar at 90° C.

Yield: 48.6 g (43.5% of theory) Decomposition >300 ° C. Elemental analysis: C 12.1%; H 2.5%; N 2.1%; P 1.5% (found) C 11.2%; H 2.7%; N 1.6%; P 1.2% (calculated)

Preparation Example 3

Compound (5)

A hot solution, at about 50° C., of 27.4 g (0.15 mol) of NaPF$_6$ in 150 ml of deionized water was added to 40.0 g (0.15 mol) of a 60% strength by weight aqueous diallylammonium chloride solution at 50° C., and the mixture was heated to 80° C. After 15 minutes, it was allowed to cool, and the volume was doubled by addition of 200 ml of an aqueous 1 normal KCl solution. After cooling to 0° C., the solid was filtered off with suction and washed with cold water until free form chloride. The substance was then dried in vacuo under 200 mbar at 90° C.

Yield: 14.1 g (50% of theory) Decomposition >260° C. Elemental analysis: C 35.1%; H 5.6%; N 5.0%; P 11.3% (found) C 35.4%; H 5.9%; N 5.1%; P 11.4%; F 42.0% (calculated)

Use Example 1

1.0 part of compound (4) were incorporated homogeneously into 99.0 parts of toner binder ("®Dialec S-309" from Diamond Shamrock, styrene/methacrylate copolymer 60:40) by means of a kneader for 45 minutes. The mixture was then ground on a universal laboratory mill and subsequently graded on a centrifugal sifter. The desired particle fraction (4 to 25 μm) was activated with a carrier of magnetite particles, coated with styrene/methacrylate copolymer 90:10, 50 to 200 μm in size of the type "90 μm Xerographic Carrier" from Plasma Materials Inc. (Manchester, N.H., USA).

The measurement was carried out on a customary q/m measuring stand. By using a sieve having a mesh width of 25 μm, it was ensured that no carrier could be carried along when the toner was blown out. The measurements were carried out at about 20° C. and 50% relative atmospheric humidity. The following q/m values [μC/g] were measured as a function of the activation time:

| Activation time | Charging g/m [μC/g] |
|---|---|
| 10 min | −19 |
| 30 min | −18 |
| 2 h | −15 |
| 24 h | −15 |

Use Examples 2 and 3

In each case 1 part of compounds (5) and (7), corresponding to Use Examples 2 and 3, were incorporated homogeneously into in each case 99 parts of toner binder as described in Use Example 1. The following q/m values [μC/g] were measured as a function of the activation time:

| Activation time | Charging g/m [μC/g] | |
|---|---|---|
| Use Example | 2 | 3 |
| 10 min | +3 | −5 |
| 30 min | +5 | −10 |
| 2 h | +2 | −16 |
| 24 h | +2 | −20 |

Use Example 4

1 part of compound (4) was incorporated homogeneously into 99 parts of a powder coating binder based on a carboxyl-containing polyester resin, for example ®Crylcoat 430 from UCB/Belgium, as described in Use Example 1. The following q/m values [μC/g] were measured as a function of the activation time, a carrier coated with PTFE (polytetrafluoroethylene) being used instead of the carrier coated with styrene/acrylate described in Use Example 1:

| Activation time | g/m [μC/g] |
|---|---|
| 10 min | +3 |
| 30 min | +4 |
| 2 h | +7 |
| 24 h | +6 |

To determine the deposition rate, 30 g of the test powder coating were sprayed under a defined pressure through a tribogun as described above. By determining the difference in weight, the amount of powder coating deposited could be determined and a deposition rate in % could be defined, and, by the charge transfer, a current flow (μA) could be measured.

| Pressure [bar] | Current [μA] | Deposition rate [%] |
|---|---|---|
| 3 | 1.4–1.8 | 52 |

Comparison Example 1

For measurement of the pure resin binder Dialec 309, the procedure was as in Use Example 1, but without kneading in additives.

| Activation time | g/m [μC/g] |
|---|---|
| 10 min | −4 |
| 30 min | −12 |
| 2 h | −27 |
| 24 h | −48 |

Comparison Example 2

For determination of the charging properties of the pure powder coating resin component Crylcoat 430, the procedure was as in Comparison Example 1, a carrier coated with PTFE (polytetrafluoroethylene) being used instead of the magnetite carrier.

| Activation time | g/m [µC/g] |
|---|---|
| 10 min | −17 |
| 30 min | −19 |
| 2 h | −19 |
| 24 h | −18 |

For determination of the deposition rate, the procedure was as in Use Example 5.

| Pressure [bar] | Current [µA] | Deposition rate [%] |
|---|---|---|
| 3 | 0.1 | 5 |

Comparison Example 3

For determination of the triboelectric charging properties of a comparable polymeric ionic ammonium compound, the procedure was as in Use Example 5:

| Activation time | g/m [µC/g] |
|---|---|
| 10 min | −8 |
| 30 min | −8 |
| 2 h | −9 |
| 24 h | −10 |

For determination of the characteristic data on triboelectric powder paint spraying of a comparable polymeric ammonium compound, the procedure was as in Use Example 5.

| Pressure [bar] | Current [µA] | Deposition rate [%] |
|---|---|---|
| 3 | 0.7–0.9 | 18 |

A comparison both with the pure powder coating resin component (Comparison Example 2) and with a comparable polymeric ammonium compound (Comparison Example 3; the preparation of the polymeric ammonium compound employed is described in CA-A-2,051,788, Preparation Example 2) significantly shows a clear improvement in the deposition rate by using the ionic diallylammonium monomer according to the invention.

We claim:

1. An electrostatically charge—improved solid state polymer dispersion comprising an ionic monomeric diallylammonium compound of the formula (I)

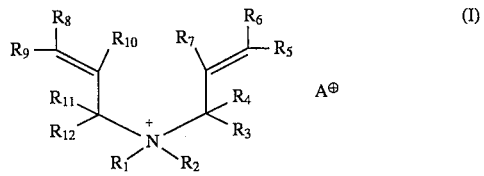

or mixture or mixed crystal thereof, in which the radicals $R_1$ to $R_{12}$ independently of one another are each a hydrogen atom, a halogen atom, a hydroxyl radical, a primary, secondary or tertiary amino radical, a carboxylic acid or carboxylic acid ester radical, an acyl radical, a sulfonic acid or sulfonic acid ester radical, a cyano radical or a nitro radical, or are in each case a radical based on an aliphatic or aromatic hydrocarbon, which is optionally interrupted by hetero atoms, and $A^\ominus$ is in each case the stoichiometric equivalent of an inorganic anion, of an anion of a heteropolyacid or of a borate of the formula (II)

in which the radicals $R_{13}$ to $R_{16}$ on the borate anion independently of one another are aliphatic or cycloaliphatic radicals, or aryl or heteroaryl or aralkyl radicals, these radicals being unsubstituted or substituted by alkyl($C_1$–$C_4$), alkoxy($C_1$–$C_4$) or aryl radicals or by halogen atoms, or are fluorine atoms, or of an organic anion, or $A^\ominus$ is a combination of these anions; or a mixture of such compounds and mixed crystals with mixed anions or cations or with mixed anions and cations, and further comprising a common polymer binder system.

2. A dispersion as claimed in claim 1, wherein the organic anion is one based on a phenolate, olefinic, aliphatic or aromatic carboxylate, sulfonate, thiolate or sulfate, in which the alkyl, alkenyl or aryl radicals optionally are perfluorinated, or based on a disulfo-pyrrolidinium-betaine of the formula (III)

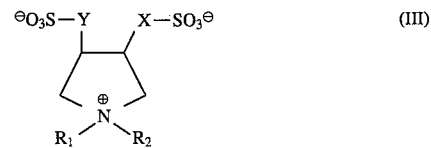

in which $R_1'$ and $R_2'$ have the meanings given for $R_1$ and $R_2$, and X and Y are in each case a straight-chain or branched aliphatic, saturated or unsaturated alkyl($C_1$–$C_{18}$) radical or alkoxy($C_1$–$C_{18}$) radical.

3. A dispersion as claimed in claim 1, wherein the anion $A^\ominus$ is an organic anion from the group consisting of $F^-$, $I^-$, $NO_3^-$, $OH^-$, $HSO_4^-$, $S_2^-$, $SO_3^{2-}$, $S_2O_3^{2-}$, $HCO_3^-$, $CO_3^{2-}$, $H_2PO_4^-$, $H_2PO_4^{2-}$, $PO_4^{3-}$, $CN^-$, cyanate, isocyanate, thiocyanate, zinc tetracyanate, zinc tetrathiocyanate, perchlorate, $PF_6^-$, $MoO_4^{2-}$, $MoS_4^{2-}$, and $WO_4^{2-}$, or a combination thereof.

4. A dispersion as claimed in claim 3, wherein the anion $A^\ominus$ is a combination of the anions mentioned with $Cl^-$, $Br^-$ or $SO_4^{2-}$ or with $Cl^-$, $Br^-$ and $SO_4^{2-}$.

5. A dispersion as claimed in claim 1, wherein the anion $A^\ominus$ is an anion of a heteropolyacid.

6. A dispersion as claimed in claim 1, wherein the $A^\ominus$ is $P(Mo_3O_{10})_4^{3-}$, $P(W_3O_{10})_4^{3-}$ or a silicomolybdate.

7. A dispersion as claimed in claim 1, wherein the anion $A^\ominus$ is a borate.

8. A dispersion as claimed in claim 1, wherein the anion $A^\ominus$ is tetrafluoroborate, tetrachloroborate, tetraphenylborate, tetra(fluorophenyl)borate, tetra(chlorophenyl)borate, tetratolylborate, tetranaphthylborate, tetra(methoxyphenyl)borate, tetrabiphenylborate, tetrabenzylborate or tetrapyridyl-borate, or a combination thereof.

9. A dispersion as claimed in claim 1, wherein the anion $A^\ominus$ is an organic anion from the group consisting of ethylsulfate, phenolate, nitrophenolate, thiolate, acetate, lactate, benzoate, the mono- or dianion of dithiobenzoic acid, salicylate, 2-hydroxy-3-naphthoate, 2-hydroxy-6-naphthoate, ethylsulfonate, phenylsulfonate, tosylate, perfluoroacetate, perfluoro-$C_1$-$C_{30}$-alkylbenzoate, perfluoroethylsulfonate, perfluoro-$C_1$-$C_{30}$-alkylbenzenesulfonate and saturated or unsaturated aliphatic or cycloaliphatic or aromatic di- and tricarboxylate or di- or trisulfonate, oxalate or succinate.

10. A dispersion as claimed in claim 1, wherein the anion $A^\ominus$ is a disulfopyrrolidinium-betaine of the formula (III), in which $R_1'$ and $R_2'$ are $R_1$ and $R_2$, and X and Y are straight-chain or branched aliphatic, saturated or unsaturated alkyl($C_1$-$C_{18}$) or alkoxy($C_1$-$C_{18}$) radicals or polyoxyalkylene radicals of the formula (alkylene($C_2$-$C_5$)—O)$_n$—R, in which R is a hydrogen atom or an alkyl($C_1$-$C_4$) radical and n is a number from 1 to 10.

11. A dispersion as claimed in claim 10, wherein X and Y are alkyl($C_1$-$C_5$) or alkoxy($C_1$-$C_5$) radicals or polyoxyethylene or polyoxypropylene radicals of the formula (alkylene($C_2$-$C_5$)—O)$_n$—R, in which R is a hydrogen atom or an alkyl($C_1$-$C_4$) radical and n is a number from 1 to 10.

12. A dispersion as claimed in claim 1, wherein the anion $A^\ominus$ is an anion from the group consisting of $F^-$, $I^-$, $BF_4^-$, $B(aryl)_4^-$, $PF_6^-$ or $P(Mo_3O_{10})_4^{3-}$, or of a disulfo-pyrrolidinium-betaine of the formula (III);

$R_1$ and $R_2$ and $R_1'$ and $R_2'$ independently of one another are hydrogen atoms, straight-chain or branched, saturated or unsaturated alkyl($C_1$-$C_{18}$) or alkoxy($C_1$-$C_{18}$) radicals, polyoxyalkylene radicals of the formula (alkylene($C_1$-$C_5$)—O)$_n$—R, in which R is a hydrogen atom, an alkyl($C_1$-$C_4$) radical or an acyl radical and n is a number from 1 to 10; aryl or heteroaryl radicals, aralkyl radicals; aralkoxy radicals; alkaryl radicals or cycloalkyl radicals, or the above-mentioned radicals contain at least one hetero atom and are unsubstituted or substituted by one or more carboxamide radicals, sulfonamide radicals, urethane radicals, ketone radicals, primary, secondary or tertiary amino radicals, nitro radicals, ether radicals, alkyl($C_1$-$C_4$) radicals, alkoxy($C_1$-$C_4$) radicals, aroxy radicals, halogenoalkyl($C_1$-$C_{30}$) radicals, halogenoalkoxy($C_1$-$C_{30}$) radicals or ester radicals, one or more halogen atoms or hydroxyl, carboxyl, sulfonic acid, cyano or mercapto groups, or a combination thereof, or $R_1$ and $R_2$, and $R_1'$ and $R_2'$ together form a saturated or unsaturated, aromatic or non-aromatic 5- or 7-membered ring system, which optionally contains further hetero atoms in the ring, and which is unsubstituted or substituted or modified by condensation of or bridging to other ring systems, or which is unsubstituted or substituted and modified by condensation of or bridging to another ring systems;

and $R_3$ to $R_{12}$ independently of one another have the meanings given above for $R_1$ and $R_2$, and $R_1'$ and $R_2'$ or are halogen atoms or aroxy radicals.

13. A dispersion as claimed in claim 12, wherein $R_1$ and $R_2$, and $R_1'$ and $R_2'$ independently of one another are polyoxyethylene or polyoxypropylene radicals or a combination thereof of the formula (alkylene($C_2$-$Cl_3$)—O)$_n$—R, in which R is an acetyl, benzoyl or naphthoyl radical; phenyl, naphthyl or pyridyl radicals, tolyl radicals, methoxyphenyl radicals, benzyl radicals, cyclopentyl or cyclohexyl radicals; or the above-mentioned radicals contain at least one nitrogen, oxygen, sulfur or phosphorus atom or a combination thereof; and are substituted by one or more phenoxy radicals, alkylene($C_2$-$C_4$)-O-alkyl($C_1$-$C_4$) radicals, —C(O)O-alkyl-($C_1$-$C_4$) radicals or a combination thereof, or $R_1$ and $R_2$, and $R_1'$ and $R_2'$ together form a pyridinium ring system, which optionally contains nitrogen, oxygen, sulfur or a combination thereof as hetero atoms; and $R_3$ to $R_{12}$ are phenoxy radicals.

14. A dispersion as claimed in claim 13, wherein $R_1$ and $R_2$, and $R_1'$ and $R_2'$ together form a morpholinium ring system or a quinolinium ring system.

15. A dispersion as claimed in claim 1, wherein $A^\ominus$ is an anion from the group consisting of $BF_4^-$ and $B(aryl)_4^-$, in which aryl is phenyl, naphthyl, fluorophenyl, chlorophenyl, methoxyphenyl, biphenyl, pyridyl or tolyl or a combination thereof;

$R_1$ and $R_2$ independently of one another are hydrogen atoms, straight-chain or branched, saturated or unsaturated alkyl($C_1$-$C_8$) or alkoxy($C_1$-$C_8$) radicals, aryl or heteroaryl radicals, aralkyl radicals, aralkoxy radicals, alkaryl radicals, or cycloalkyl radicals, the radicals $R_1$ and $R_2$ being unsubstituted or being substituted by one or more halogen atoms, hydroxyl, carboxyl, sulfonic acid or carboxamide radicals, sulfonamide radicals, keto radicals, primary, secondary or tertiary amino radicals, nitro radicals, ether radicals, aroxy radicals, halogenoalkyl($C_1$-$C_4$) radicals, halogenoalkoxy($C_1$-$C_4$) radicals or ester radicals, and $R_3$ to $R_{12}$ independently of one another have the meanings given above for $R_1$ and $R_2$, or are halogen atoms.

16. A dispersion as claimed in claim 15, wherein $R_1$ and $R_2$ independently of one another are phenyl, naphthyl, pyridyl, tolyl, methoxyphenyl, benzyl, cyclopentyl or cyclohexyl radicals, the radicals $R_1$ and $R_2$ being unsubstituted or substituted by one or more radicals of the group consisting of —NH—C(O)-alkyl ($C_1$-$C_4$), —NH—$SO_2$-alkyl($C_1$-$C_4$), —C(O)-alkyl($C_1$-$C_4$), —$NH_2$, —NH[alkyl($C_1$-$C_4$)], —N[alkyl($C_1$-$C_4$)]$_2$, alkylene-($C_2$-$C_4$)—O-alkyl($C_1$-$C_4$), alkyl($C_1$-$C_4$), alkoxy($C_1$-$C_4$), phenoxy and —C(O)—O-alkyl($C_1$-$C_4$).

17. A dispersion as claimed in claim 1, wherein $A^\ominus$ has the meaning $BF_4^-$, $B(phenyl)_4^-$, or disulfo-pyrrolidinium-betaine of the formula (III), in which $R_1'$ and $R_2'$ have the meanings given below for $R_1$ and $R_2$, $R_1$ is hydrogen or methyl, $R_2$ is hydrogen, methyl or octyl, and $R_3$ to $R_{12}$ are in each case hydrogen.

18. The dispersion as claimed in claim 1, wherein $A^\ominus$ is chloride, bromide or the stoichiometric equivalent of sulfate.

19. The dispersion as claimed in claim 1, wherein the ionic monomeric diallyammonium compound is present in an amount of 0.01 to 30% by weight.

20. The dispersion as claimed in claim 19, wherein the ionic monomeric diallyammonium compound is present in an amount of 0.1 to 5% by weight.

21. The dispersion as claimed in claim 1, comprising an electrophotographic toner or developer for copying or duplicating masters and for printing electronically, magnetically or optically stored information or in colorproofing.

22. The dispersion as claimed in claim 1, comprising a powder or paint for surface coating of objects of metal, wood, plastics, glass, ceramic, concrete, textile material, paper or rubber.

23. The dispersion as claimed in claim 1, comprising a triboelectrically or electrokinetically sprayed powder coating.

* * * * *